United States Patent
Chen et al.

(10) Patent No.: US 11,583,171 B2
(45) Date of Patent: Feb. 21, 2023

(54) SURFACE-MOUNT DEVICE PLATFORM AND ASSEMBLY

(71) Applicant: OmniVision Technologies, Inc., Santa Clara, CA (US)

(72) Inventors: Teng-Sheng Chen, Hsinchu (TW); Chien-Chan Yeh, Changhua County (TW); Cheng-Fang Chiu, Hsinchu (TW); Wei-Feng Lin, Hsinchu (TW)

(73) Assignee: OmniVision Technologies, Inc., Santa Clara, CA (US)

( * ) Notice: Subject to any disclaimer, the term of this patent is extended or adjusted under 35 U.S.C. 154(b) by 292 days.

(21) Appl. No.: 16/548,753

(22) Filed: Aug. 22, 2019

(65) Prior Publication Data

US 2021/0052134 A1    Feb. 25, 2021

(51) Int. Cl.
*H05K 1/11*    (2006.01)
*H05K 3/46*    (2006.01)
*A61B 1/005*    (2006.01)

(52) U.S. Cl.
CPC ............ *A61B 1/0055* (2013.01); *H05K 1/118* (2013.01); *H05K 2201/10151* (2013.01)

(58) Field of Classification Search
CPC .................. H05K 1/118; H05K 1/189; H05K 2201/10151; H05K 2201/0278; H05K 3/4691; H05K 1/0278; A61B 1/005; A61B 1/0008; A61B 1/0011; A61B 1/051
See application file for complete search history.

(56) References Cited

U.S. PATENT DOCUMENTS

| | | |
|---|---|---|
| 2005/0056457 A1 | 3/2005 | Gall et al. |
| 2007/0099483 A1* | 5/2007 | Tsai ................ H05K 1/118 439/492 |
| 2008/0047737 A1* | 2/2008 | Sahara .............. H05K 1/186 29/830 |
| 2008/0111907 A1 | 5/2008 | Ito et al. |
| 2010/0014265 A1* | 1/2010 | Sagisaka ........... H05K 3/4691 361/784 |
| 2010/0065313 A1* | 3/2010 | Takeuchi ........... H05K 3/4691 174/258 |
| 2011/0304016 A1* | 12/2011 | Nakamura ........ H01L 21/4857 257/532 |

(Continued)

*Primary Examiner* — Roshn K Varghese
(74) *Attorney, Agent, or Firm* — Lathrop GPM LLP

(57) ABSTRACT

A surface-mount device platform includes a surface-mounting region, a connection region, and a bendable region therebetween, each including a respective part of a base substrate. The base substrate includes electrically-conductive layers interspersed with electrically-insulating build-up layers. Each of the surface-mounting region, the connection region, and the bendable region spans between a bottom substrate-surface and a top substrate-surface of the base substrate. The surface-mounting region further includes an electrically-insulating first top rigid-layer, and device bond-pads exposed on a top surface of the first top rigid-layer facing away from the top substrate-surface in the surface-mounting region. The connection region further includes an electrically-insulating second top rigid-layer and a plurality of connector bond-pads each exposed on a top surface of the second top rigid-layer facing away from the top substrate-surface in the connection region, and electrically connected to a respective device bond-pad via at least one of the electrically conductive layers.

21 Claims, 5 Drawing Sheets

(56) References Cited

U.S. PATENT DOCUMENTS

| | | | |
|---|---|---|---|
| 2014/0091428 A1* | 4/2014 | Hossain | H01L 23/5389 |
| | | | 257/532 |
| 2014/0353014 A1* | 12/2014 | Lai | H05K 3/4691 |
| | | | 174/254 |
| 2015/0378144 A1 | 12/2015 | Handte et al. | |
| 2017/0135216 A1* | 5/2017 | Cho | H05K 1/113 |
| 2019/0116664 A1* | 4/2019 | Krivec | H05K 3/4691 |
| 2019/0321613 A1* | 10/2019 | Jones | A61K 31/7088 |
| 2020/0305289 A1* | 9/2020 | Yu | H05K 3/4682 |
| 2021/0045235 A1* | 2/2021 | Tuominen | H05K 3/4691 |
| 2021/0186311 A1* | 6/2021 | Levy | A61B 1/00114 |

\* cited by examiner

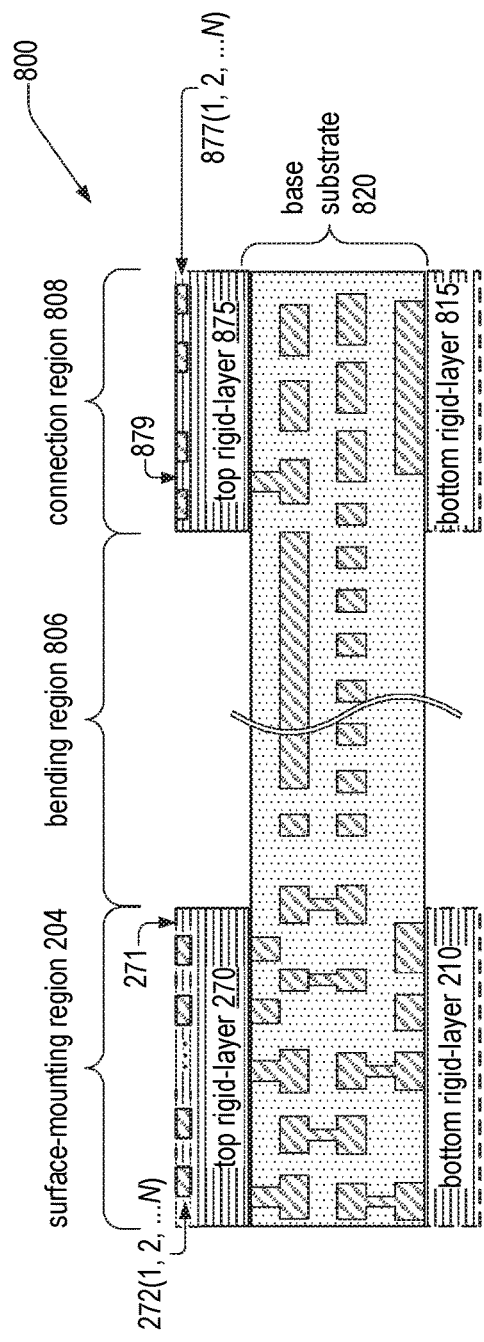
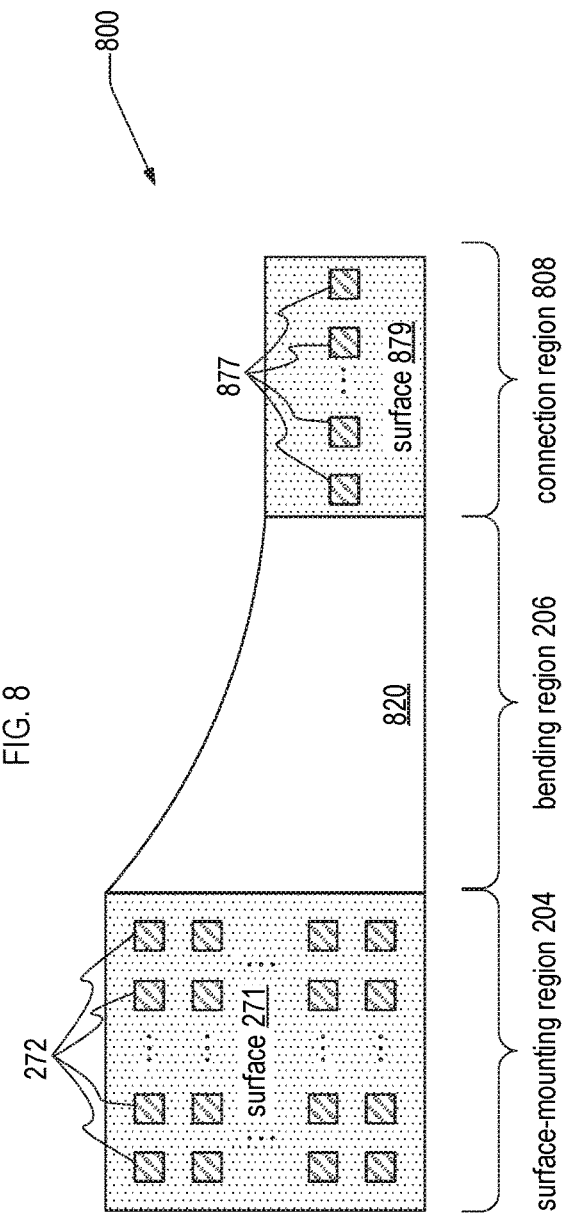

SURFACE-MOUNT DEVICE PLATFORM AND ASSEMBLY

BACKGROUND

An endoscope is a medical diagnostic instrument used for viewing a ventricle within a patient. A flexible imaging endoscope includes a flexible shaft capable of being inserted into the patient through an orifice thereof. The shaft has a tip that includes a light source and a camera for respectively illuminating and capturing images of part of the patient, such as a body cavity or an organ.

FIG. 1 is a cross-sectional schematic of a ventricle 190 having a lesion 192 imaged by an end-view endoscope 110. Lesion 192 is on a ventricle sidewall 191. Ventricle 190 has a ventricle diameter 190D in the cross-section of FIG. 1, and is for example a portion of an esophagus or an intestine. Endoscope 110 has a shaft width 112. To image ventricle sidewall 191 perpendicularly, end-view endoscope 110 must bend at the tip so its width within ventricle 190 is width 114, which exceeds width 112. Width 114, which depends in part on shaft width 112, places a lower limit on ventricle diameter 190D of ventricles 190 that end-view endoscope 110 can safely image or even enter.

End-view endoscope 110 includes a camera 130 electrically connected to a plurality of wires 124. Cost, yield, and robustness of end-view endoscope 110 is determined in part by how camera 130 is electrically connected to wires 124.

SUMMARY OF THE EMBODIMENTS

In an embodiment, a surface-mount device platform includes a surface-mounting region, a connection region, and a bendable region therebetween, each including a respective part of a base substrate. The base substrate includes a plurality of electrically conductive layers interspersed with a plurality of electrically-insulating build-up layers. Each of the surface-mounting region, the connection region, and the bendable region spans between a bottom substrate-surface and a top substrate-surface of the base substrate. The surface-mounting region further includes, on the top substrate-surface, (i) an electrically-insulating first top rigid-layer and (ii) a plurality of device bond-pads exposed on a top surface of the first top rigid-layer facing away from the top substrate-surface in the surface-mounting region. The connection region further includes, on the top substrate-surface, (i) an electrically-insulating second top rigid-layer and (ii) a plurality of connector bond-pads each (a) exposed on a top surface of the second top rigid-layer facing away from the top substrate-surface in the connection region and (b) electrically connected to a respective one of the plurality of device bond-pads via at least one of the plurality of electrically conductive layers.

BRIEF DESCRIPTION OF THE FIGURES

FIG. 8 is a cross-sectional view and FIG. 9 is a plan view of a surface-mount device platform, in an embodiment.

DETAILED DESCRIPTION OF THE EMBODIMENTS

Figure 1:
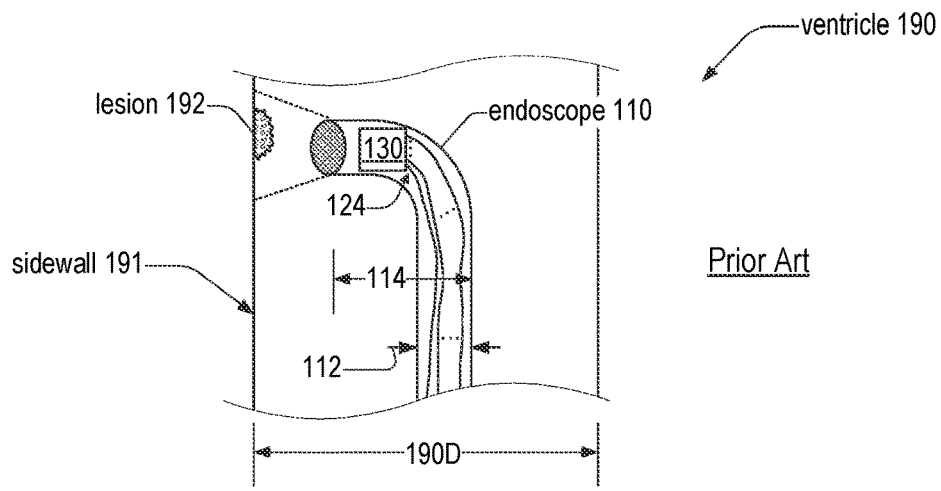
FIG. 1 is a cross-sectional schematic of a ventricle that includes a lesion imaged by an endoscope, in an embodiment.
Figure 2:
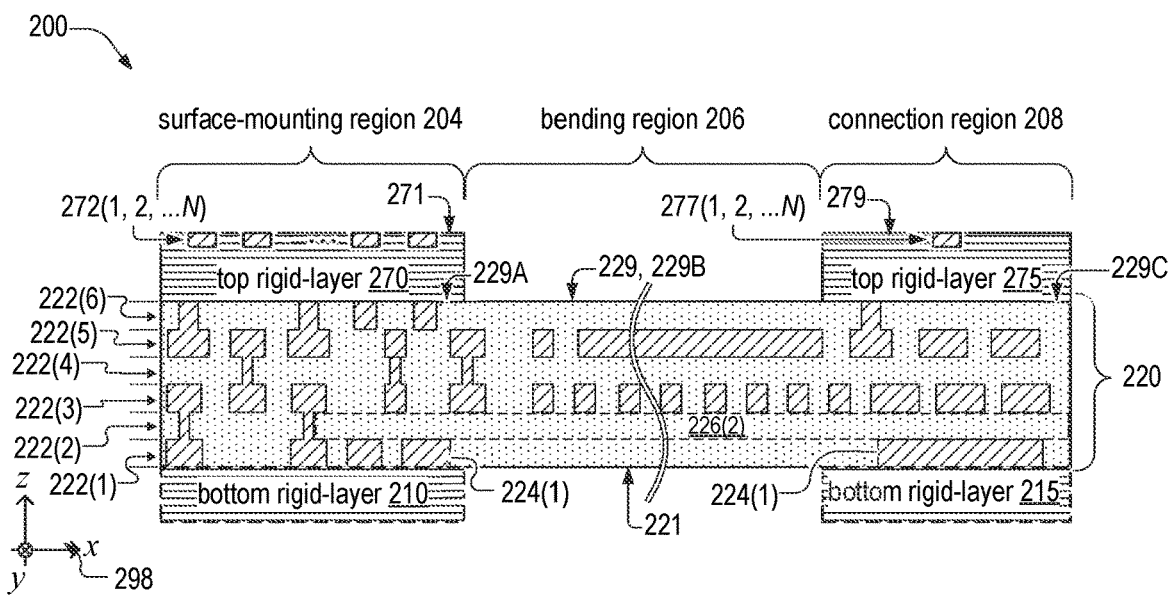
FIG. 2 is a cross-sectional view and FIG. 3 is a plan view of a surface-mount device platform, in an embodiment.
Figure 3:
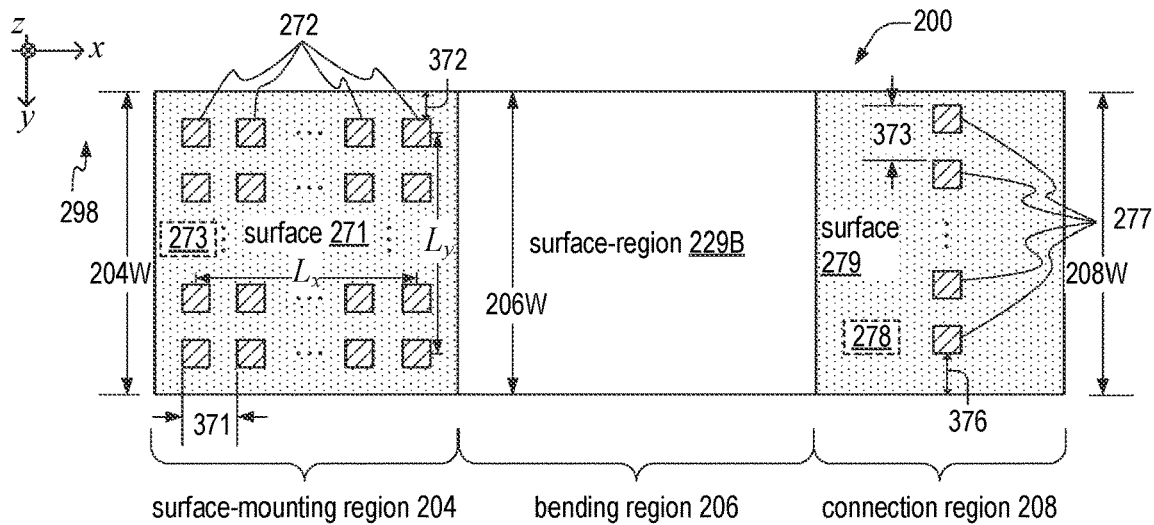

FIG. 2 is a cross-sectional view and FIG. 3 is a plan view of a surface-mount device platform 200. FIGS. 2 and 3 are best viewed together in the following description. 2 and 3 include a coordinate system 298 that defines orthogonal axes x, y, and z. Herein, reference to an axis x, y, or z or associated direction ±x, ±y, or ±z refers to coordinate system 298. Also, herein, a horizontal plane is parallel to the x-y plane, a width refers to an objects extension in the y direction, and vertical refers to the z direction. The cross-sectional vim of FIG. 2 is in a plane that is parallel to the x-z plane. The plan view of FIG. 3 is in a plane that is parallel to the x-y plane.

Surface-mount device platform 200 includes a base substrate 220, which includes (i) a plurality of conductive layers 224 interspersed with a plurality of electrically insulating build-up layers 226, and (ii) a surface-mounting region 204, a connection region 208, and a bendable region 206 therebetween, each spanning between a bottom substrate-surface 221 and a top substrate-surface 229 of base substrate 220. In embodiments, base substrate 220 is a coreless substrate, such as a coreless ball-grid array (BGA) substrate.

Base substrate 220 includes M layers 222 each defined by a respective height range above bottom substrate surface 221. A conductive layer 224 and a build-up layer 226 within one layer 222(k) is referred to as conductive layer 224(k) and build-up layer 226(k), respectively, where k is a positive integer less than or equal to M. For example, conductive layers 224 include conductive layer 224(1) and build-up layers 226 include build-up layer 226(2). In FIG. 2, reference numerals 224(1) and 226(2) denote parts of conductive layer 224(1) and build-up layer 226(2), respectively. For clarity of illustration, not all conductive layers 224 and build-up layers 226 are labelled in FIG. 2.

While M equals six in the embodiment of FIG. 3, base substrate 220 may include fewer than or more than seven layers. In embodiments, each layer 222 has a respective thickness between ten and twenty micrometers, which may correspond to a thickness of a build-up layer 226 and/or a conductive layer 224. A conductive layer 224 within a same plane with a build-up layer 226 may be thinner than the build-up layer 226. In embodiments, one or more conductive layers 224 have a thickness between ten and twenty micrometers. In embodiments, at least two of layers 222 have the same thickness.

In embodiments, within bendable region 206, each of surfaces 221 and 229 lack any exposed conductive areas, such that they are entirely electrically insulating within bendable region 206. FIG. 2 denotes the regions of top substrate-surface 229 within regions 204, 206, and 208 as surface-regions 229A, 229B, and 229C, respectively.

Surface-mounting region 204 includes, on surface-region 229A, a top rigid-layer 270 and a plurality of device bond-pads 272(1, 2, . . . , N). Top rigid-layer 270 has a top surface 271 facing away from surface-region 229A. Each bond-pad 272 is exposed on top surface 271. In embodiments, each bond-pad 272 extends through rigid-layer 270 and electrically connects to a respective conductive path of conductive layer 224. Top rigid-layer 270 is formed of an electrical insulator, which, in embodiments, has a higher flexural modulus than the electrical insulator that constitutes build-up layers 226. Each device bond-pad 272 may be either a solder-mask defined (SMD) pad, e.g., when layer 270 is formed via an additive process, or a non-solder mask defined (NSMD) pad, e.g., when layer 270 is formed via a subtractive process.

Connection region 208 also includes, on surface-region 229C, a top rigid-layer 275 and a plurality of connector bond-pads 277(1, 2, . . . , N). Top rigid-layer 275 has a top surface 279 facing away from surface-region 229C. Each connector bond-pad 277(k) is exposed on top surface 279 and is connected to a respective device bond-pad 272(k) via a conductive layer 224, where k≤N and is a positive integer. Top rigid-layer 275 is formed of an electrical insulator that has a higher flexural modulus than the electrical insulator that constitutes build-up layers 226. In embodiments, each connector bond-pad 277 is a laser-soldering pad. Top rigid-layers 270 and 275 may be formed of the same material.

A first conductive layer 224 and a second conductive layer 224 may be electrically connected by a third conductive layer 224, or a via, located at least in part between the first and second conductive layers 224. A plurality of conductive layers 224 may form conductive paths between each of a plurality of bond-pad pairs 272(k) and 277(k). Each patterned conductive layer 224 may include a plurality of coplanar conductive paths electrically insulated from one another, e.g., by a build-up layer 226 coplanar with the conductive layer 224.

In embodiments, surface-mounting region 204 includes a bottom rigid-layer 210 and connection region 208 includes a bottom rigid-layer 215. In such embodiments, the part of base substrate 220 within surface-mounting region 204 is between layers 210 and 270, and the part of base substrate 220 within connection region 208 is between layers 215 and 275. Each of bottom rigid-layers 210 and 215 is formed of an electrical insulator that has a higher flexural modulus than the electrical insulator that constitutes build-up layers 226.

In embodiments, each of layers 226, 270, and 275 are formed of epoxy molding compounds. In embodiments, rigid-layers 210 and 215 are formed of the same material and/or rigid-layers 270 and 275 are formed of the same material. All of rigid-layers 210, 215, 270, and 275 may be formed of the same material. In embodiments, each conductive layer 224 is formed of copper, and each build-up layer 226 is formed of one of a dielectric, thermoset resin, a thermoplastic polymer, an epoxy molding compound, and a silica-filled epoxy.

Spacing of device bond-pads 272 may be constrained to accommodate surface-mountable devices, such as camera modules, with ball-grid arrays having horizontal dimensions less than 600 micrometers by 600 micrometers. Accordingly, in embodiments, bond-pads 272 form a rectangular array having dimensions $L_x \times L_y$, where each of $L_x$ and $L_y$ are less than or equal to 600 micrometers. Each of dimensions $L_x$ and $L_y$ may correspond to respective center-to-center distances between maximally separated bond-pads 272 in the x and y directions.

Adjacent device bond-pads 272 are separated by a distance 371, which may be between 75 micrometers and 350 micrometers. Adjacent connector bond-pads 277 are separated by a distance 373, which may be between 75 micrometers and 350 micrometers. In embodiments, a minimum distance 372 between any device bond-pad 272 and an edge top rigid-layer 270 is between 100 micrometers and 200 micrometers. The aforementioned upper limits of 373 and 372 correspond to representative minimum distances for flexible printed circuit design rules.

In embodiments, a minimum distance 376 between any connector bond-pad 277 and an edge top rigid-layer 275 is also between 100 micrometers and 200 micrometers. Regions 204, 206, and 208 have respective widths 204W, 206W, and 208W. While FIG. 3 illustrates widths 204W, 206W, and 208W being equal, each of widths 204W, 206W, and 208W may have a different respective width without departing from the scope of the embodiments. In embodiments, width 204W may exceed at least one of width 206W and 208W, for example, to accommodate surface-mounting of multiple devices on surface-mounting region 204. In embodiments, the multiple devices include a sensor and at least one light-emitting diode.

In embodiments, rigid-layer 270 includes additional device bond-pads 273 which may accommodate an additional surface-mount device, such as one or more light-emitting diodes. In embodiments, surface-mount device platform 200 includes a surface-mount device electrically connected to device bond-pads 272, and at least one additional surface-mount device electrically connected to device bond-pads 273. When rigid-layer 270 includes additional bond-pads 273, top rigid-layer 275 may include additional connection bond-pads 278 each electrically connected to a respective device bond-pad 273.

Figure 4:
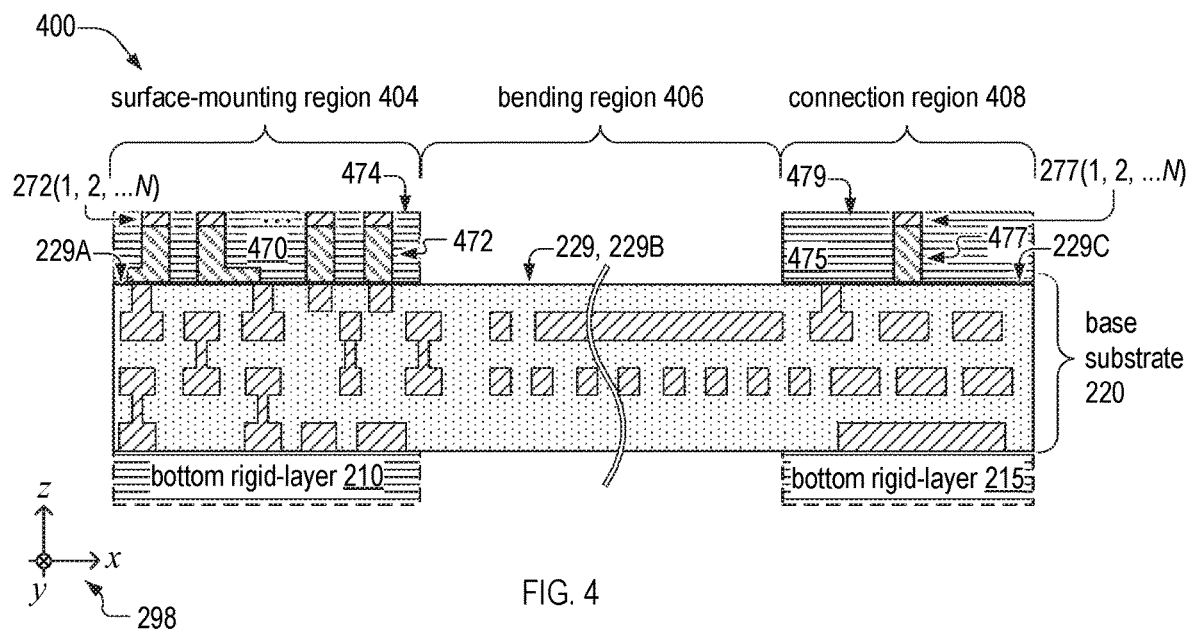
FIG. 4 is a cross-sectional view of a surface-mount device platform, which is an example of the surface-mount device of FIG. 2, in an embodiment.

FIG. 4 is a cross-sectional view of a surface-mount device platform 400. Surface-mount device platform 400 is an example of surface-mount device platform 200. Surface-mount device platform 400 includes regions 404, 406, and 408, which are examples of regions 204, 206, and 208, respectively. Surface-mount device platform 400 also includes top rigid-layers 470 and 475, which are respective examples of rigid-layers 270 and 275 and have respective top surfaces 474 and 479.

Surface-mounting region 404 includes N conductive elements 472 located between surface-region 229A and bond-pads 272. Each conductive element 472 electrically connects a respective bond-pad 272 to a conductive layer 224 via a conductive path through top rigid layer 470. In embodiments, each conductive element 472: (a) is part of a patterned conductive layer, (b) is a via, (c) extends at least partially through a plurality of holes through top rigid-layer 470, or (d) is any combination thereof. In embodiments, each bond-pad 272 extends through top rigid-layer 470, such that each conductive element 472 is part of respective bond-pad 272.

Connection region 408 includes N conductive elements 477 located between surface-region 229C and bond-pads 277. Each conductive element 477 electrically connects a respective bond-pad 277 to a conductive layer 224 via a conductive path through top rigid layer 475. In embodiments, each conductive element 477: (a) is part of a patterned conductive layer, (b) is a via, (c) extends at least partially through a plurality of holes through top rigid-layer 475, or (d) is any combination thereof. In embodiments, each bond-pad 277 extends through rigid-layer top 470, such that each conductor of conductive layer 477 is part of respective bond-pad 277.

Figure 5:
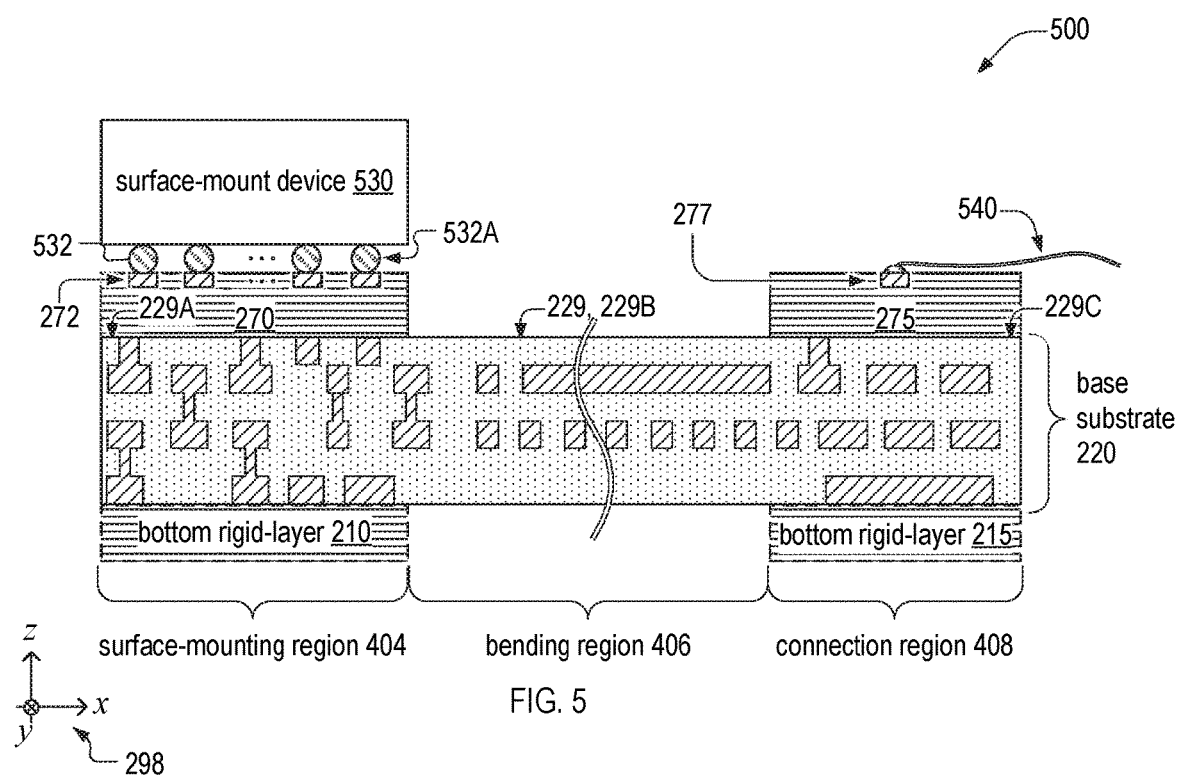
FIG. 5 is a cross-sectional view of a surface-mount-device assembly that includes the platform of FIG. 2, in an embodiment.

FIG. 5 is a cross-sectional view of a surface-mount-device assembly 500, which includes a surface-mount device 530 surface-mounted on surface-mount device platform 200. Camera 130 is an example of surface-mount device 530. In embodiments, surface-mount device 530 includes one of a photodetector, an image sensor, a CMOS camera module, a microphone, a vibration sensor, and a thermometer. Surface-mount device 530 includes a ball grid array 532A, which includes a plurality of solder balls 532 each electrically connected to a respective device bond-pad 272. Surface-mount-device assembly 500 may include a micro-cable 540 electrically connected to each connector bond-bad 277.

Figure 6:
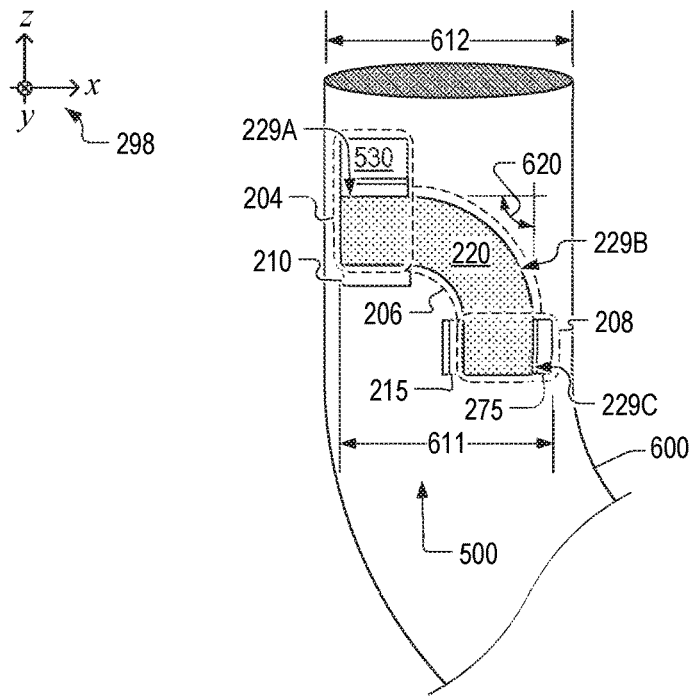
FIG. 6 is a cross-sectional view of surface-mount-device assembly of FIG. 5 in a bent configurated, in an embodiment.

FIG. 6 is a cross-sectional view of surface-mount-device assembly 500 within an endoscope enclosure 600. In the configuration of FIG. 6, in which bendable region 206 is bent such that respective planes of surface-regions 229A and 229B are not parallel, and intersect at an angle 620. In embodiments, angle 620 is between eighty and ninety degrees. In embodiments, bendable region 206 has a radius of curvature between 0.2 mm and 1.0 mm. In embodiments, a ratio of the radius of curvature of bendable region 206 to a thickness of substrate 220 is between eight and twelve.

When bent as shown in FIG. 6, surface-mount-device assembly 500 with surface-mount device 530 thereon has a width 611. In embodiments, width 611 is less than a width 612 of endoscope enclosure 600. Width 612 is analogous to width 112 of endoscope 110. In FIG. 6, neither the thickness or radius of curvature of base substrate 220 is illustrated to scale with respect to width 612.

Figure 7:
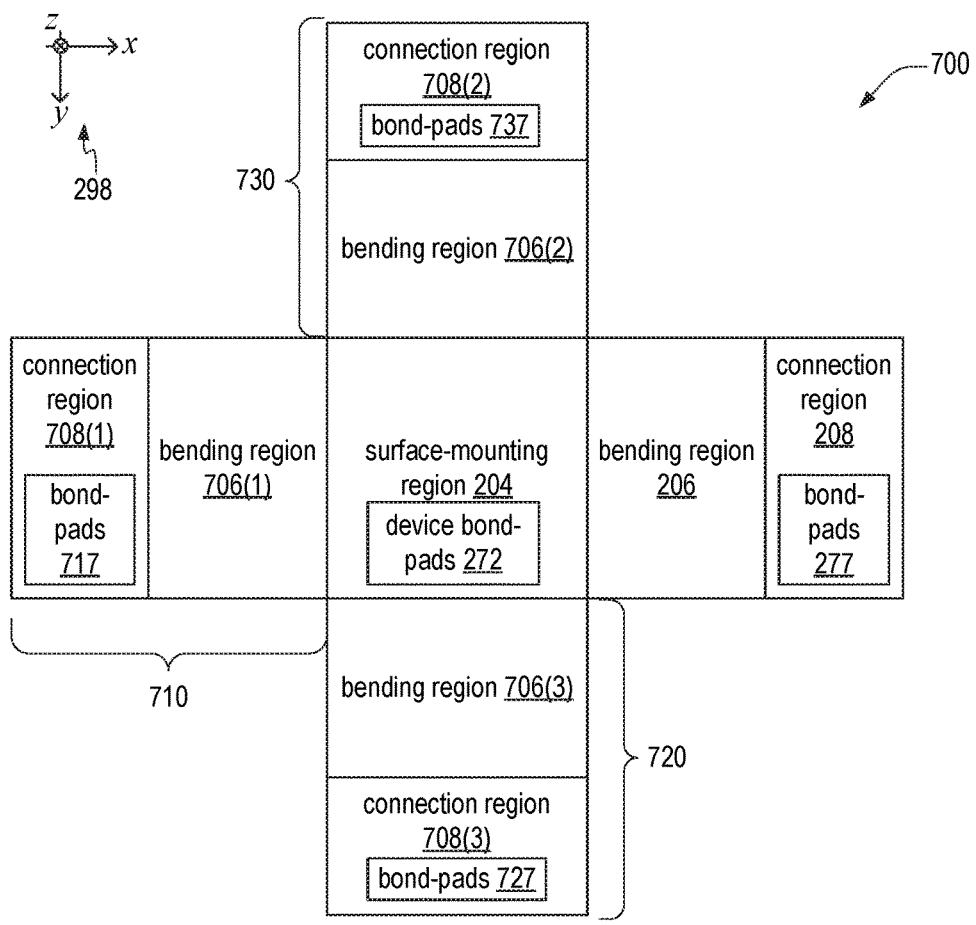
FIG. 7 is a plan view of a substrate surface-mount device, which is an example of the substrate of FIG. 2, in an embodiment.

FIG. 7 is a plan view of a substrate 600, which is an example of surface-mount device platform 200. Substrate 700 includes surface-mounting region 204, bendable region 206, and connection region 208 of surface-mount device platform 200. Substrate 600 also includes at least one of extensions 710, 720, and 730, which include respective bendable regions 706(1,2,3) and respective connection regions 708(1,2,3). Each bendable region 706 is an example of bendable region 206. Each connection region 708 is an example of connection region 208, and provides additional bond-pads electrically connected to device bond-pads 272 such that the number of device bond pads 272 may exceed the number of bond pads 277. Connection regions 708(1,2, 3) have a respective plurality of connector bond-pads 717, 727, and 737, each of which are examples of connector bond-pads 277. Each device bond-pad 272 of surface-mounting region 204 is electrically connected to either one connector bond-pad 277, one connector bond-pad 717, one connector bond-pad 727, or one connector bond-pad 737.

FIG. 8 is a cross-sectional view and FIG. 9 is a plan view of a surface-mount device platform 800. FIGS. 8 and 9 are best viewed together in the following description. Surface-mount device platform 800 is an example of surface-mount device platform 200 and includes top rigid-layer 270 thereof. Surface-mount device platform 800 includes base substrate 820, which is an example of base substrate 220. Surface-mount device platform 800 also includes top rigid-layer 875, which is an example of top rigid-layer 275. In embodiments surface-mount device platform 800 includes bottom rigid-layer 815, which is an example of bottom rigid-layer 215. Top rigid-layer 875 has a top surface 879.

In surface-mount device platform 800, connection region 208 is implemented as a connection region 808, where the width of connection region 808 (y direction) differs from that of surface-mounting region 204. Accordingly, base substrate 802 has a non-uniform width within bendable region 806, as shown in FIG. 9.

Figure 10:
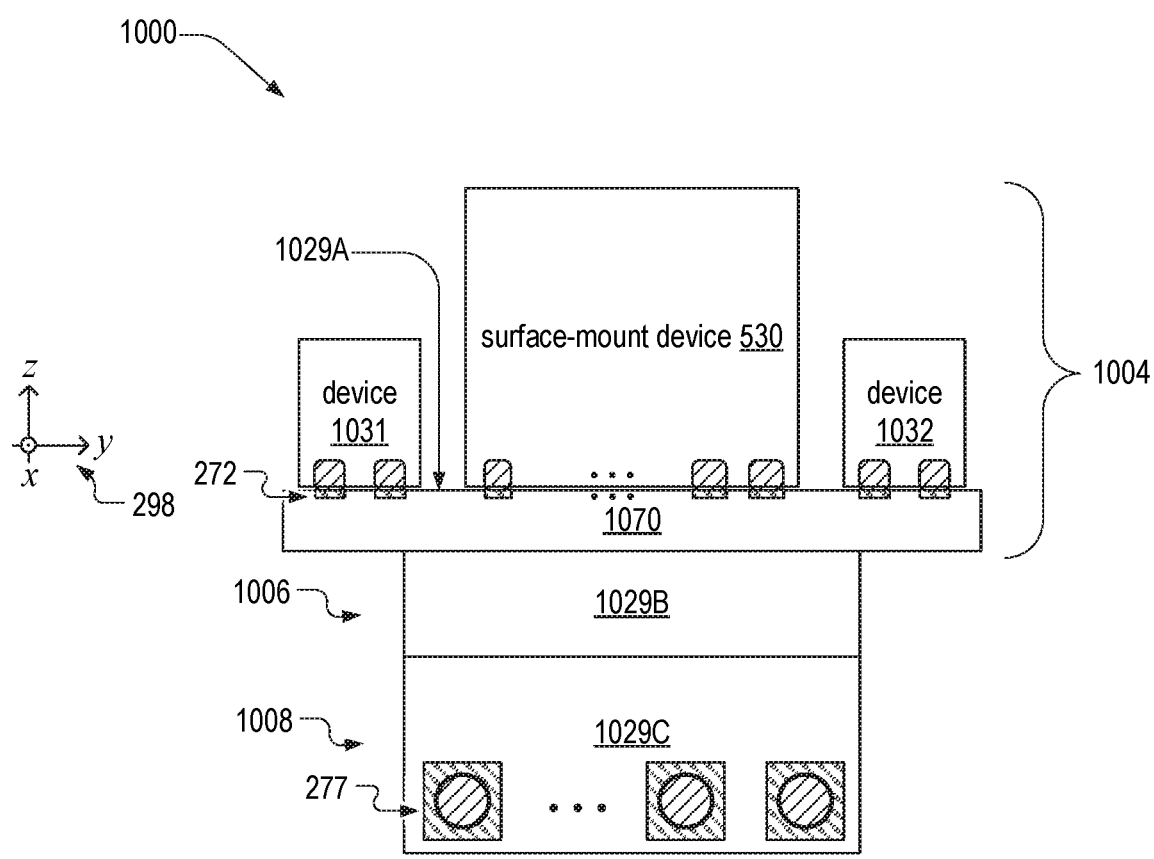
FIG. 10 is a cross-sectional view of a surface-mount-device assembly, which is an example of the surface-mount-device assembly of FIG. 5.

FIG. 10 is a cross-sectional view of a surface-mount-device assembly 1000. Surface-mount-device assembly 1000 is an example of surface-mount-device assembly 500, FIG. 5 when bendable region 406 is bent about an axis perpendicular to the x-z plane, as in FIG. 6. Whereas the cross-sectional plane of FIG. 5 is parallel to the x-z plane, the cross-sectional view of FIG. 10 is parallel to the y-z plane. Hence, a cross-sectional view of surface-mount-device assembly 1000 in the x-z plane may be identical to the cross-sectional view of surface-mount-device assembly 500 in FIG. 6.

Surface-mount-device assembly 1000 includes surface-mounting region 1004, bendable region 1006, and connection region 1008, which are respective examples of regions 404, 406, and 408. For clarity of illustration, FIG. 10 illustrates only parts of bendable region 1006 that are parallel to the y-z plane.

Surface-mounting region 1004 includes, in addition to surface-mount device 530, additional surface-mount devices 1031 and 1032. At least one of surface-mount devices 1031 and 1032 may be a light-emitting diode. Each of surface-mount device 530 and surface-mount devices 1031 and 1032 is surface-mounted to a respective plurality of device bond-pads 272. Surface-mount-device assembly 1000 includes a rigid-layer 1070, which is an example of rigid-layer 270 that includes device bond-pads 272 that accommodate each of devices 530, 1031, and 1032.

Surface-mount-device assembly 1000 includes a base substrate, not illustrated in FIG. 10, which is an example of base substrate 220. The base substrate of assembly 1000 includes conductive layers configured to electrically connect each of devices 530, 1031, and 1032, via device bond-pads 272, to connector bond-pads 277 of connection region 1008. Base substrate 1010 has a top surface 1029, which has corresponding surface regions 1029A, 1029B, and 1029C. Top surface 1029 and regions 1029A, 1029B, and 1029C are respective examples of surface 229 and surface-regions 229A, 229B, and 229C. For clarity of illustration, FIG. 10 denotes surface regions 1029A, 1029B, 1029C while not denoting surface 1029.

Combinations of Features

Features described above as well as those claimed below may be combined in various ways without departing from the scope hereof. The following enumerated examples illustrate some possible, non-limiting combinations:

(A1) A surface-mount device platform includes a surface-mounting region, a connection region, and a bendable region therebetween, each including a respective part of a base substrate. The base substrate includes a plurality of electrically conductive layers interspersed with a plurality of electrically-insulating build-up layers. Each of the surface-mounting region, the connection region, and the bendable region spans between a bottom substrate-surface and a top substrate-surface of the base substrate. The surface-mounting region further includes, on the top substrate-surface, (i) an electrically-insulating first top rigid-layer and (ii) a plurality of device bond-pads exposed on a top surface of the first top rigid-layer facing away from the top substrate-surface in the surface-mounting region. The connection region further includes, on the top substrate-surface, (i) an electrically-insulating second top rigid-layer and (ii) a plurality of connector bond-pads each (a) exposed on a top surface of the second top rigid-layer facing away from the top substrate-surface in the connection region and (b) electrically connected to a respective one of the plurality of device bond-pads via at least one of the plurality of electrically conductive layers.

(A2) In any surface-mount device (A1), the surface-mounting region may further include a first patterned conductive layer, between the top substrate-surface and the plurality of device bond-pads, and electrically connecting each of the plurality of device bond-pads to one of the plurality of electrically conductive layers.

(A3) In any surface-mount device (A1) or (A2), the connection region may further include a second patterned conductive layer, between the top substrate-surface and the plurality of connector bond-pads, and electrically connecting each of the plurality of connector bond-pads to one of the plurality of electrically conductive layers (A4) In any surface-mount device (A1)-(A3), (i) the surface-mounting region may further include an electrically-insulating first bottom rigid-layer, each of the bottom substrate-surface and the top substrate-surface being between the first bottom rigid-layer and the first top rigid-layer, and (ii) the connection region may further include an electrically-insulating second bottom rigid-layer, each of the bottom substrate-surface and the top substrate-surface being between the second bottom rigid-layer and the second top rigid-layer.

(A5) In any surface-mount device (A1)-(A4), a distance between any two adjacent device bond-pads of the plurality of device bond-pads may be between 75 micrometers and 350 micrometers; and a distance between any two adjacent connector bond-pads of the plurality of connector bond-pads may be between 75 micrometers and 350 micrometers.

(A6) In any surface-mount device (A1)-(A5), on the top surface of the first top rigid-layer, a minimum distance between any of the plurality of device bond-pads and an edge of the first top rigid-layer may be between 100 micrometers and 200 micrometers; and on a top surface of the second top rigid-layer facing away from the top substrate-surface in the connection region, a minimum distance between any of the plurality of connector bond-pads and an edge of the second top rigid-layer may be between 100 micrometers and 200 micrometers.

(A7) In any surface-mount device (A1)-(A6), the plurality of device bond-pads may form a rectangular array having length and a width each less than 0.6 millimeters.

(A8) In any surface-mount device (A1)-(A7), a thickness of each of the plurality of build-up layers may be between twenty micrometers and forty micrometers.

(A9) In any surface-mount device (A1)-(A8), each of the plurality of connector bond-pads may be a laser-soldering pad.

(A10) In any surface-mount device (A1)-(A9), each of the plurality of build-up layers, the first top rigid-layer, and the second top rigid-layer may be formed of an epoxy molding compound.

(A11) In any surface-mount device (A1)-(A10), each of the first top rigid-layer and the second top rigid-layer may have a higher flexural modulus than each of the plurality of build-up layers.

(A12) In any surface-mount device (A1)-(A11), each of the plurality of build-up layers may be formed of a first epoxy molding compound having a first flexural modulus, each of the first top rigid-layer and the second top rigid-layer may be formed of an epoxy second molding compound having a flexural modulus that exceeds the first flexural modulus.

(B1) A surface-mount device assembly includes any of surface-mount device (A1)-(A11), a surface-mount device, in which a ball grid array thereof includes a plurality of conductive elements each electrically connected to a respective one of the plurality of device bond-pads.

(B2) In any surface-mount device assembly (B1), the surface-mount device may include a sensor electrically connected to each of the plurality of conductive elements.

(B3) In any surface-mount device assembly (B2), the sensor may include a photodetector.

(B4) In any surface-mount device assembly (B2), the sensor may be an image sensor.

(B5) In any surface-mount device assembly (B2), the sensor may include one of a microphone, a vibration sensor, and a thermometer.

Changes may be made in the above surface-mount device platforms and surface-mount device assemblies without departing from the scope hereof. It should thus be noted that the matter contained in the above description or shown in the accompanying drawings should be interpreted as illustrative and not in a limiting sense. Herein, and unless otherwise indicated, the phrase "in embodiments" is equivalent to the phrase "in certain embodiments," and does not refer to all embodiments. The following claims are intended to cover all generic and specific features described herein, as well as all statements of the scope of the present platforms and assemblies, which, as a matter of language, might be said to fall therebetween.

What is claimed is:

1. A surface-mount device platform comprising:
    a surface-mounting region, a connection region, and a bendable region therebetween, each including a respective part of a base substrate;
    the base substrate including a plurality of electrically conductive layers interspersed with a plurality of electrically-insulating build-up layers, each of the surface-mounting region, the connection region, and the bendable region spanning between a bottom substrate-surface and a top substrate-surface of the base substrate, each of the bottom and the top substrate-surfaces being entirely insulating within the bendable region;
    the surface-mounting region further including, on the top substrate-surface, (i) an electrically-insulating first top rigid-layer and (ii) a plurality of device bond-pads that are (i) exposed on a top surface of the first top rigid-layer facing away from the top substrate-surface in the surface-mounting region and (iii) directly above the base substrate; and
    the connection region further including, on the top substrate-surface, (i) an electrically-insulating second top rigid-layer and (ii) a plurality of connector bond-pads each (a) exposed on a top surface of the second top rigid-layer facing away from the top substrate-surface in the connection region, (b) electrically connected to a respective one of the plurality of device bond-pads via at least one of the plurality of electrically conductive layers, and (c) directly above the base substrate,
    each of the first top rigid-layer and the second top rigid-layer having a higher flexural modulus than each of the plurality of build-up layers.

2. The surface-mount device platform of claim 1, the surface-mounting region further including a first patterned conductive layer, between the top substrate-surface and the plurality of device bond-pads, and electrically connecting each of the plurality of device bond-pads to one of the plurality of electrically conductive layers.

3. The surface-mount device platform of claim 1, the connection region further including a second patterned conductive layer, between the top substrate-surface and the plurality of connector bond-pads, and electrically connecting each of the plurality of connector bond-pads to one of the plurality of electrically conductive layers.

4. The surface-mount device platform of claim 1,
the surface-mounting region further including an electrically-insulating first bottom rigid-layer, each of the bottom substrate-surface and the top substrate-surface being between the first bottom rigid-layer and the first top rigid-layer; and
the connection region further including an electrically-insulating second bottom rigid-layer, each of the bottom substrate-surface and the top substrate-surface being between the second bottom rigid-layer and the second top rigid-layer.

5. The surface-mount device platform of claim 1,
a distance between any two adjacent device bond-pads of the plurality of device bond-pads being between 75 micrometers and 350 micrometers; and
a distance between any two adjacent connector bond-pads of the plurality of connector bond-pads being between 75 micrometers and 350 micrometers.

6. The surface-mount device platform of claim 1,
on the top surface of the first top rigid-layer, a minimum distance between any of the plurality of device bond-pads and an edge of the first top rigid-layer being between 100 micrometers and 200 micrometers; and
on a top surface of the second top rigid-layer facing away from the top substrate-surface in the connection region, a minimum distance between any of the plurality of connector bond-pads and an edge of the second top rigid-layer being between 100 micrometers and 200 micrometers.

7. The surface-mount device platform of claim 1, the plurality of device bond-pads forming a rectangular array having length and a width each less than 0.6 millimeters.

8. The surface-mount device platform of claim 1, a thickness of each of the plurality of build-up layers being between ten micrometers and twenty micrometers.

9. The surface-mount device platform of claim 1, each of the plurality of build-up layers, the first top rigid-layer, and the second top rigid-layer being formed of an epoxy molding compound.

10. The surface-mount device platform of claim 1, each of the plurality of build-up layers being formed of a first epoxy molding compound having a first flexural modulus, each of the first top rigid-layer and the second top rigid-layer being formed of a second epoxy molding compound having a flexural modulus that exceeds the first flexural modulus.

11. A surface-mount device assembly comprising:
the surface-mount device platform of claim 1; and
a surface-mount device, a ball grid array thereof including a plurality of conductive elements each electrically connected to a respective one of the plurality of device bond-pads.

12. The surface-mount device assembly of claim 11, the surface-mount device including a sensor electrically connected to each of the plurality of conductive elements.

13. The surface-mount device assembly of claim 12, the sensor including a photodetector.

14. The surface-mount device assembly of claim 12, the sensor being an image sensor.

15. The surface-mount device assembly of claim 12, the sensor including one of a microphone, a vibration sensor, and a thermometer.

16. An endoscope comprising:
an endoscope enclosure; and
the surface-mount device platform of claim 1 that is (i) within the endoscope enclosure and (ii) bent such that a width of the surface-mount device platform, spanning between the surface-mounting region and the connection region, is less than a width of the endoscope enclosure.

17. The endoscope of claim 16, an angle between the surface-mounting region and the connection region being between eighty and ninety degrees.

18. The surface-mount device platform of claim 1,
the bendable region having a thickness equal to a distance between the bottom substrate-surface and a bottom surface of one of the first and second top rigid-layers.

19. The surface-mount device platform of claim 1, the bottom substrate-surface having no electrically-insulating rigid-layers thereon.

20. A surface-mount device platform comprising:
a surface-mounting region, a connection region, and a bendable region therebetween, each including a respective part of a base substrate;
the base substrate including a plurality of electrically conductive layers interspersed with a plurality of electrically-insulating build-up layers, each of the surface-mounting region, the connection region, and the bendable region spanning between a bottom substrate-surface and a top substrate-surface of the base substrate, each of the bottom and the top substrate-surfaces being entirely insulating within the bendable region;
the surface-mounting region further including, on the top substrate-surface, (i) an electrically-insulating first top rigid-layer and (ii) a plurality of device bond-pads exposed on a top surface of the first top rigid-layer facing away from the top substrate-surface in the surface-mounting region; and
the connection region further including, on the top substrate-surface, (i) an electrically-insulating second top rigid-layer and (ii) a plurality of connector bond-pads each (a) exposed on a top surface of the second top rigid-layer facing away from the top substrate-surface in the connection region, and (b) electrically connected to a respective one of the plurality of device bond-pads via at least one of the plurality of electrically conductive layers,
each of the first top rigid-layer and the second top rigid-layer having a higher flexural modulus than each of the plurality of build-up layers,
the bendable region having a thickness equal to a distance between the bottom substrate-surface and a bottom surface of one of the first and second top rigid-layers.

21. The surface-mount device platform of claim 20, the bottom substrate-surface having no electrically-insulating rigid-layers thereon.

* * * * *